United States Patent [19]

Weber et al.

[11] 4,297,354
[45] Oct. 27, 1981

[54] SUBSTITUTED 4-AMINO-2,6-DIARYL-TETRAHYDROTHIO-PYRANS AND SALTS THEREOF, AND USE AS ANTIDEPRESSANTS

[75] Inventors: Karl-Heinz Weber, Gau-Algesheim; Claus Schneider, Ingelheim am Rhein; Gerhard Walther, Bingen am Rhein; Karl-Heinz Pook; Karin Böke, both of Ingelheim am Rhein; Wolf D. Bechtel, Appenheim, all of Fed. Rep. of Germany

[73] Assignee: Boehringer Ingelheim GmbH, Ingelheim am Rhein, Fed. Rep. of Germany

[21] Appl. No.: 216,423

[22] Filed: Dec. 15, 1980

[30] Foreign Application Priority Data

Dec. 21, 1979 [DE] Fed. Rep. of Germany ....... 2951634

[51] Int. Cl.³ ................. A61K 31/38; A61K 31/445; C07D 335/02
[52] U.S. Cl. ............................. 424/248.51; 424/250; 424/268; 424/275; 544/144; 544/145; 544/374; 544/379; 546/207; 546/214; 549/28
[58] Field of Search ................. 549/28; 546/207, 214; 544/145, 146, 374, 379; 424/248.51, 250, 275, 268

[56] References Cited

PUBLICATIONS

Baliah et al., Indian Journal of Chemistry, vol. 16B, (1978), pp. 776–778.

Primary Examiner—Richard Raymond
Attorney, Agent, or Firm—Hammond & Littell, Weissenberger & Muserlian

[57] ABSTRACT

Compounds of the steroisomeric formulas

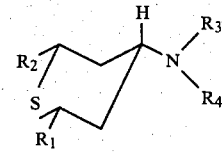

and

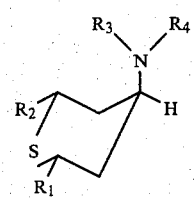

wherein
$R_1$ and $R_2$, which may be identical to or different from each other, are each phenyl, substituted phenyl, thienyl or furyl;
$R_3$ is hydrogen or straight or branched alkyl of 1 to 3 carbon atoms; and
$R_4$ is straight or branched alkyl of 1 to 3 carbon atoms; or
$R_3$ and $R_4$, together with each other and the nitrogen atom to which they are attached, form a piperidino, 4-amino-piperidino, 4-(lower alkylamino)-piperidino, piperazino, 4-(alkyl of 1 to 2 carbon atoms)-piperazino or morpholino radical; and nontoxic, pharmacologically acceptable acid addition salts thereof. The compounds as well as their salts are useful as antidepressants.

13 Claims, No Drawings

SUBSTITUTED 4-AMINO-2,6-DIARYL-TETRAHYDROTHIOPYRANS AND SALTS THEREOF, AND USE AS ANTIDEPRESSANTS

This invention relates to novel substituted 4-amino-2,6-diaryl-tetrahydrothiopyrans and non-toxic acid addition salts thereof, to methods of preparing these compounds, to pharmaceutical compositions containing them as active ingredients, and to methods of using them as antidepressants.

More particularly, the present invention relates to a novel class of tetrahydrothiopyrans represented by the stereoisomeric formulas

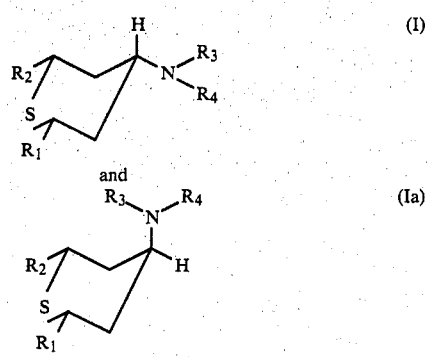

wherein $R_1$ and $R_2$, which may be identical to or different from each other, are each phenyl, substituted phenyl, thienyl or furyl;

$R_3$ is hydrogen or straight or branched alkyl of 1 to 3 carbon atoms; and $R_4$ is straight or branched alkyl of 1 to 3 carbon atoms; or $R_3$ and $R_4$, together with each other and the nitrogen atom to which they are attached, form a piperidino, 4-amino-piperidino, 4-(lower alkyl-amino)-piperidino, piperazino, 4-(alkyl of 1 to 2 carbon atoms)-piperazino or morpholino radical;

and non-toxic, pharmacologically acceptable acid addition salts thereof.

The term "substituted phenyl" is intended to designate mono-, di- and tri-substituted phenyl, where the substituents are halogen, methyl or methoxy.

The novel compounds of the present invention may be prepared by the following methods:

Method A

By reducing a tetrahydrothiopyranone of the formula

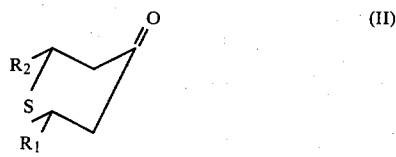

wherein $R_1$ and $R_2$ have the same meanings as in formulas I and Ia, with a reducing agent such as lithium aluminum hydride, sodium borohydride or sodium cyanoborohydride, whereby a mixture of two stereoisomeric carbinols of the formulas

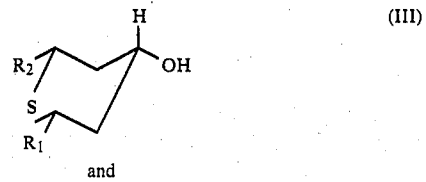

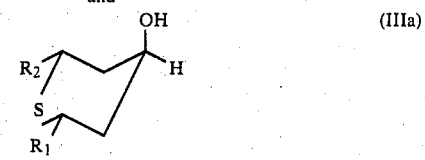

wherein $R_1$ and $R_2$ have the same meanings as in formulas I and Ia, is obtained. This mixture of carbinols is esterified in conventional manner, preferably with a p-toluenesulfonyl halide or a methanesulfonic acid halide, and the mixture of stereoisomeric esters thus obtained is subsequently reacted with a primary or secondary amine of the formula

wherein $R_3$ and $R_4$ have the same meanings as in formulas I and Ia.

Method B

For the preparation of those end products of the formula I or Ia wherein the amino substituent in the 4-position is acyclic, by reacting a tetrahydrothiopyranone of the formula II with a mixture of formic acid and an amine of the formula IV, wherein $R_3$ is hydrogen or alkyl of 1 to 3 carbon atoms, at low temperatures, preferably at 0° to −10° C.

These end products may also be prepared by reacting an acyclic amine of the formula IV with a tetrahydrothiopyranone of the formula II in the presence of hydrogen and a catalyst such as palladium or Raney nickel, or in the presence of a complex hydride such as sodium borohydride, lithium aluminum hydride or sodium cyanoborohydride.

Likewise, they may also be prepared by alkylating a 4-amino-2,6-diaryl-tetrahydrothiopyran of the formula

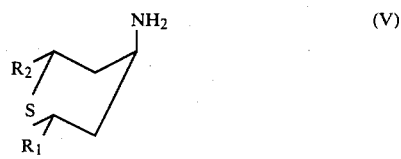

wherein $R_1$ and $R_2$ have the same meanings as in formulas I and Ia, with an alkyl halide or a dialkyl sulfate.

The starting compounds of the formula II may be obtained by reacting an optionally substituted benzalacetone (1) with an aldehyde (2), and subjecting the reaction product (3) to ring closure with hydrogen sulfide in ethanol/sodium acetate, pursuant to the following reaction sequence:

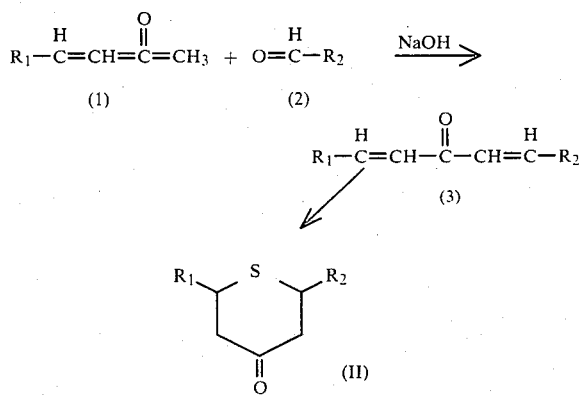

The starting compounds of the formula V, some of which are disclosed by V. Baliah et al., Ind. J. Chem. Soc. B 16 (1978), 9, 776, are readily accessible by reduction of the corresponding tetrahydrothiopyranone-oximes.

As indicated by formulas I and Ia, the compounds of the present invention occur in two stereoisomeric forms because the amino substitutent in the 4-position can be in the equatorial (e) or axial configuration (a). The spatially demanding substitutents in the 2- and 6-positions of the tetrahydrothiopyran ring are in equatorial configuration, as shown by the proton spectra.

Although the separation of the stereoisomers can be effected in a prior stage, it is preferred not to separate the stereoisomers until the end product stage. The separation is carried out in conventional manner, that is, either chromatographically or by fractional crystallization.

The compounds of the formulas I and Ia are basic and therefore form addition salts with inorganic and organic acids. Examples of non-toxic, pharmacologically acceptable acid addition salts are those formed with hydrohalic acids, sulfuric acid, phosphoric acid, aminosulfonic acid, formic acid, acetic acid, propionic acid, lactic acid, glycolic acid, gluconic acid, maleic acid, succinic acid, tartaric acid, benzoic acid, salicylic acid, citric acid, ascorbic acid, p-toluenesulfonic acid or oxyethanesulfonic acid.

The following examples illustrate the present invention and will enable others skilled in the art to understand it more completely. It should be understood, however, that the invention is not limited solely to the particular examples given below.

EXAMPLE 1

4a- and 4e -Dimethylamino-2-(4-chloro-phenyl)-6-phenyl-tetrahydrothiopyran by method B.

0.036 mol (11 gm) of 2-(4-chloro-phenyl)-6-phenyl-tetrahydrothiopyranone-(4) were dissolved in 60 ml of dimethylformamide, and then a solution of dimethylamino formate (prepared from 3.2 gm of formic acid and 12.6 gm of dimethylamine at $-10°$ C.) was added dropwise at 20° C. The resulting mixture was refluxed for 4 hours while stirring, cooled to 10° C., admixed with 50 ml of ether, and carefully acidified to pH 2 with 2 N hydrochloric acid. The aqueous phase was neutralized with sodium hydroxide and repeatedly extracted with ether. The combined ether extracts were dried and evaporated, the residue was charged into an $SiO_2$-column, and the column was eluted with a mixture of methylene chloride/methanol (99:1), yielding 3 gm of the 4a-dimethylamino-compound having a melting point of 115° C.

The methanol content of the eluant was now increased to 5%, whereby 1.2 gm of the 4e-dimethylamino-compound having a melting point of 69°–70° C. was obtained.

The total yield of 4a- and 4e-dimethylamino-isomers was 35% of theory.

The tetrahydrothiopyranone starting material was prepared as follows:

0.14 mol (20 gm) of benzalacetone and 0.14 mol of p-chloro-benzaldehyde were dissolved in 250 ml of ethanol, 20 ml of 10% sodium hydroxide were added, and the mixture was vigorously stirred for one hour at about 10° C. Thereafter, the precipitated yellow crystals were collected by suction filtration, washed with a little water, and recrystallized from isopropanol, yielding 25.2 gm (68.5% of theory) of a light yellow crystalline substance having a melting point of 133° C. (cf. intermediate compound 3 of the reaction sequence above). 0.1 mol (25 gm) of this compound and 0.34 mol (27.8 gm) of sodium acetate were suspended in 700 ml of 90% ethanol and, while stirring and refluxing, a vigorous stream of hydrogen sulfide was passed through the suspension for four hours. Thereafter, the solvent was distilled off, the residue was taken up in a mixture of water and methylene chloride, and the methylene chloride phase was separated, dried and evaporated. The residue was charged into an $SiO_2$-column, the column was eluted with methylene chloride, the eluates were evaporated, and the residue was caused to crystallize with isopropyl ether. 40% of theory (11.2 gm) of 2-(4-chloro-phenyl)-6-phenyl-tetrahydrothiopyranone-(4), m.p. 124° C., were obtained.

EXAMPLE 2

4a- and 4e-(4-Methyl-piperazino)-2,6-bis(4-chloro-phenyl)-tetrahydrothiopyran by method A 0.012 mol (5 gm) of a mixture of 4a- and 4e-methanesulfonyloxy-2,6-bis(4-chloro-phenyl)-tetrahydrothiopyran was refluxed for 12 hours with 10 ml of 1-methylpiperazine. Thereafter, the excess 1-methylpiperazine was distilled off, the residue was charged into an $SiO_2$-column, and the column was eluted with methylene chloride/methanol (99:1). The first fraction yielded 1.4 gm of 4a-(4-methyl-piperazino)-2,6-bis(4-chloro-phenyl)-tetrahydrothiopyran as a viscous oil; its hydrochloride (1.3 gm), prepared by treatment of the base with ethanolic hydrochloric acid, had a melting point of 286°–288° C. The methanol content of the eluent was then increased to 5%, and the column was again eluted, yielding 1.1 gm of 4e-(4-methyl-piperazino)-2,6-bis(4-chloro-phenyl)-tetrahydrothiopyran, m.p. 159° C. The total yield of the two stereoisomers was 40% of theory.

The starting material was obtained as follows:

One half of a mixture of 50 mg of p-chloro-benzaldehyde and 10.4 gm of acetone (mol ratio 2:1) was added at room temperature to a solution of 360 ml of aqueous 10% sodium hydroxide in 280 ml of ethanol, and the mixture was stirred for 15 minutes. Thereafter, the other half of the aldehyde-ketone mixture was added, and the mixture was again stirred for 30 mintues. The yellow crystalline precipitate which had formed was collected by suction filtration, washed with water and recrystallized from a little isopropanol, yielding 50 gm (91% of theory) of the desired compound, m.p. 187°–188° C. (cf. intermediate compound 3 of the reaction sequence above).

0.16 mol (49 gm) of this intermediate and 43 gm of sodium acetate were suspended in 1 liter of 10% ethanol, and hydrogen sulfide was passed through the suspension for 4 hours while refluxing. Thereafter, the solution was concentrated by evaporation, extracted with methylene chloride, and the organic phase was dried. The solvent was then evaporated, and the residue was caused to crystallize by addition of isopropyl ether, yielding 31 gm (57% of theory) of the corresponding tetrahydrothiopyranone of the formula II, m.p. 141°–143° C.

0.05 mol (18 gm) of this tetrahydrothiopyranone were suspended in 100 ml of methanol and, while stirring, 7.4 gm (0.2 mol) of sodium borohydride were added in portions at 0° C. The mixture was stirred for two hours, whereupon the solvent was distilled off, the residue was taken up in a mixture of methylene chloride and water, and the methylene chloride phase was separated, dried and evaporated. 13.1 gm (72.4% of theory) of 2,6-bis(4-chloro-phenyl)-tetrahydrothiopyran-4a- and 4e-carbinol, m.p. 194°–195° C., were obtained.

13 gm (0.04 mol) of the mixture of isomeric carbinols and 6.9 gm (0.06 mol) of methanesulfonic acid chloride were dissolved in 100 ml of methylene chloride, 4.8 gm of pyridine were added to the solution, and the mixture was refluxed for 16 hours. After cooling, the excess methanesulfonic acid chloride was carefully decomposed with water and ammonia, and the methylene chloride phase was separated, washed with water, dried and evaporated. The residue was charged into an $SiO_2$-column and eluted with methylene chloride. The eluate yielded 14.1 gm (88% of theory) of a mixture of 4a- and 4e-methane-sulfonyloxy-2,6-bis(4-chloro-phenyl)-tetrahydrothiopyran, m.p. 196°–197° C.

Using procedures analogous to those described in Examples 1 and 2, the following compound of the formulas I and Ia were also prepared:

| Example No. | $R_1$ | $R_2$ | $R_3$ | $R_4$ | Configuration of amino-group | m.p. °C. |
|---|---|---|---|---|---|---|
| 3 | phenyl | phenyl | —CH₃ | —CH₃ | a | base 68–70 HCl salt 204–205 |
| 4 | phenyl | phenyl | —CH₃ | —CH₃ | e | 96–104 |
| 5 | 4-Cl-phenyl | 4-Cl-phenyl | —CH₃ | —CH₃ | a | 158–159 |
| 6 | 2-thienyl | 2-thienyl | —CH₃ | —CH₃ | a | 104–105 |
| 7 | 2-thienyl | 2-thienyl | —CH₃ | —CH₃ | a | 134–135 |
| 8 | 2-furyl | 2-furyl | —CH₃ | —CH₃ | a | 78–79 |
| 9 | 2-furyl | 2-furyl | —CH₃ | —CH₃ | e | 56–58 |
| 10 | 4-Cl-phenyl | phenyl | —CH₃ | —CH₃ | e | 69–70 |
| 11 | 4-Cl-phenyl | phenyl | —CH₃ | H | a | 111–112 |
| 12 | 4-Cl-phenyl | phenyl | H | —CH₃ | e | HCl salt 221–222 |
| 13 | 3-Cl-phenyl | phenyl | —CH₃ | —CH₃ | a | oil |
| 14 | 3-Cl-phenyl | phenyl | —CH₃ | —CH₃ | e | oil |
| 15 | 2-Cl-phenyl | phenyl | —CH₃ | —CH₃ | a | 67–68 |
| 16 | 4-Br-phenyl | phenyl | —CH₃ | —CH₃ | a | 107 |
| 17 | 4-Br-phenyl | phenyl | —CH₃ | —CH₃ | e | 80–81 |

-continued

| Example No. | R₁ | R₂ | R₃ | R₄ | Configuration of amino-group | m.p. °C. |
|---|---|---|---|---|---|---|
| 18 | F–C₆H₄– | C₆H₅– | –CH₃ | –CH₃ | a | 90–91 |
| 19 | F–C₆H₄– | C₆H₅– | –CH₃ | –CH₃ | e | base oil HCl salt 279–280 |
| 20 | F–C₆H₄– | F–C₆H₄– | –CH₃ | –CH₃ | a | 120–121 |
| 21 | H₃CO–C₆H₄– | C₆H₅– | –CH₃ | –CH₃ | a | 78–80 |
| 22 | H₃CO–C₆H₄– | C₆H₅– | –CH₃ | –CH₃ | e | 105–106 |
| 23 | CH₃O–C₆H₄– | CH₃O–C₆H₄– | –CH₃ | –CH₃ | a | 122–123 |
| 24 | CH₃O–C₆H₄– | CH₃O–C₆H₄– | –CH₃ | –CH₃ | e | 129 |
| 25 | 3-thienyl | C₆H₅– | –CH₃ | –CH₃ | a | 75–76 |
| 26 | 3-thienyl | C₆H₅– | –CH₃ | –CH₃ | e | HCl salt 265–266 |
| 27 | 3-thienyl | C₆H₅– | –CH₃ | H | a | HCl salt 250 |
| 28 | 3-thienyl | C₆H₅– | H | –CH₃ | e | HCl salt 245 |
| 29 | 2-thienyl | C₆H₅– | –CH₃ | –CH₃ | a | 79–80 |
| 30 | 2-thienyl | C₆H₅– | –CH₃ | –CH₃ | e | base 100–101 HCl salt 250–251 |
| 31 | 2-furyl | C₆H₅– | –CH₃ | –CH₃ | a | 52–53 |
| 32 | 2-furyl | C₆H₅– | –CH₃ | –CH₃ | e | HCl salt 215–220 |
| 33 | 3-thienyl | Cl–C₆H₄– | –CH₃ | –CH₃ | a | oil |
| 34 | 3-thienyl | Cl–C₆H₄– | –CH₃ | –CH₃ | e | base-oil HCl salt 235 |
| 35 | Cl₂–C₆H₃– | C₆H₅– | –CH₃ | –CH₃ | a | oil |
| 36 | Cl₂–C₆H₃– | C₆H₅– | –CH₃ | –CH₃ | e | oil |
| 37 | Cl–C₆H₄– | C₆H₅– | –C₂H₅ | –C₂H₅ | a | 120–121 |
| 38 | Cl–C₆H₄– | C₆H₅– | –C₂H₅ | –C₂H₅ | e | oil |

-continued

| Example No. | R$_1$ | R$_2$ | R$_3$ | R$_4$ | Configuration of amino-group | m.p. °C. |
|---|---|---|---|---|---|---|
| 39 | Cl—⟨C₆H₄⟩— | Cl—⟨C₆H₄⟩— | —CH(CH$_3$)$_2$ | H | a | 128–129 |
| 40 | Cl—⟨C₆H₄⟩— | Cl—⟨C₆H₄⟩— | H | —CH(CH$_3$)$_2$ | e | 109–110 |
| 41 | CH$_3$O—⟨C₆H₄⟩— | ⟨C₆H₅⟩— | —CH$_3$ | H | a | 115 HCl salt 232 |
| 42 | H$_3$CO—⟨C₆H₄⟩— | ⟨C₆H₅⟩— | H | —CH$_3$ | e | HCl salt 211 |
| 43 | H$_3$CO—⟨C₆H₄⟩— | H$_3$CO—⟨C₆H₄⟩— | —CH$_3$ | H | a | HCl salt 263 |
| 44 | H$_3$CO—⟨C₆H₄⟩— | H$_3$CO—⟨C₆H₄⟩— | H | —CH$_3$ | e | HCl salt 220 |
| 45 | 3,4,5-(CH$_3$O)$_3$—⟨C₆H₂⟩— | ⟨C₆H₅⟩— | —CH$_3$ | —CH$_3$ | a | 115 HCl salt 237 |
| 46 | 3,4,5-(H$_3$CO)$_3$—⟨C₆H₂⟩— | ⟨C₆H₅⟩— | —CH$_3$ | —CH$_3$ | e | 191–192 HCl salt 232 |

The compounds of the present invention, that is, those embraced by formulas I and Ia and their non-toxic, pharmacologically acceptable acid addition salts, have useful pharmacodynamic properties. More particularly, they exhibit antidepressant and tetrabenazine-antagonistic activities in warm-blooded animals, such as mice.

It is known that in various forms of depressions certain areas of the brain are impoverished in biogenic amines, especially noradrenaline and serotonin; the biogenic amine concentration in these brain areas can be increased by preventing their re-uptake into the neurons. The compounds of the present invention inhibit the re-uptake of noradrenaline and serotonin; the axial isomers primarily inhibit the re-uptake of noradrenaline, while the equatorial isomers mainly inhibit the re-uptake of serotonin.

Particularly effective antidepressants are those compounds of the formulas I and Ia where the amino substituent in the 4-position is a monoalkylamino or dialkyl-amino group. In the axial stereoisomer series of these compounds the toxicity decreases in the sequence R$_1$, R$_2$=phenyl→substituted phenyl→heteroaryl.

Especially effective are those 4-amino-substituted compounds where the 2- and/or 6-positions are substituted by substituted phenyl groups, such as 4a and 4e-dimethyl-amino-2,6bis(4-methoxy-phenyl)-tetrahydro-thiopyran, 4a- and 4e-methylamino-2,6-bis(4-methoxy-phenyl)-tetrahydrothiopyran, 4a- and 4e-dimethylamino-2-(4-chloro-phenyl)-6-phenyl-tetrahydrothiopyran and their non-toxic, pharmacologically acceptable acid addition salts.

For pharmaceutical purposes the compounds of the present invention are administered to warm-blooded animals perorally, parentally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.0014 to 0.71 mgm/kg body weight, preferably 0.0071 to 0.36 mgm/kg body weight. The daily dose is from 0.071 to 2.14 mgm/kg body weight.

The following examples illustrate a few pharmaceutical dosage unit compositions comprising a compound of the present invention as an active ingredient and represent the best modes contemplated of practicing the invention. The parts are parts by weight unless otherwise specified.

EXAMPLE 55

Coated pills

The pill core composition is compounded from the following ingredients:

| | |
|---|---|
| 4a-Dimethylamino-2-(4-chloro-phenyl)-6-phenyl-tetrahydro-thiopyran | 25.0 parts |
| Lactose | 50.0 parts |
| Corn starch | 22.0 parts |
| Gelatin | 2.0 parts |
| Magnesium stearate | 1.0 parts |
| Total | 100.0 parts |

Preparation

The active ingredient, the lactose and the corn starch are intimately admixed with each other, the mixture is moistened with an aqueous 10% solution of the gelatin, the moist mass is granulated by passing it through a 1 mm-mesh screen, and the moist granulate is dried and again passed through the screen. The dry granulate is admixed with the magnesium stearate, and the resulting composition is compressed into 100 mgm-pill cores which are subsequently coated with a thin shell consisting essentially of a mixture of sugar, titanium dioxide, talcum and gum arabic, and polished with beeswax. Each coated pill is an oral dosage unit composition containing 25 mgm of the active ingredient.

EXAMPLE 56

Tablets

The tablet composition is compounded from the following ingredients:

| | |
|---|---|
| 4a-Methylamino-2,6-bis(4-methoxy-phenyl)-tetrahydrothiopyran | 10.0 parts |
| Lactose | 40.0 parts |
| Corn starch | 44.0 parts |
| Soluble starch | 5.0 parts |
| Magnesium stearate | 1.0 parts |
| Total | 100.0 parts |

Preparation

The active ingredient and the magnesium stearate are intimately admixed with each other, the mixture is granulated by moistening it with an aqueous solution of the soluble starch and passing the moist mass through a screen, and the granulate is dried and intimately admixed with the lactose and the corn starch. The resulting composition is compressed into 100 mgm-tablets, each of which is an oral dosage unit composition containing 10 mgm of the active ingredient.

EXAMPLE 57

Suppositories

The suppository composition is compounded from the following ingredients:

| | |
|---|---|
| 4e-(4-Methyl-piperazino)-2,6-bis-(4-chloro-phenyl)-tetrahydro-thiopyran | 10.0 parts |
| Suppository base (e.g. cocoa butter) | 1,690 parts |
| Total | 1,700.0 parts |

Preparation

The finely powdered active ingredient is blended with the aid of an immersion homogenizer into the suppository base which has previously been melted and cooled to 40° C. 1700 mgm-portions of the resulting composition are poured at 35° C. into cooled suppository molds and allowed to harden therein. Each suppository is a rectal dosage unit composition containing 10 mgm of the active ingredient.

EXAMPLE 58

Hypodermic solution

The solution is compounded from the following ingredients:

| | | |
|---|---|---|
| 4a-Dimethylamino-2,6-bis(4-chloro-phenyl)-tetrahydro-thiopyran | | 5.0 parts |
| Sodium pyrosulfite | | 1.0 parts |
| Sodium salt of EDTA | | 0.5 parts |
| Sodium chloride | | 8.5 parts |
| Double-distilled water | q.s.ad | 1000.0 parts |

Preparation

The active ingredient and the excipients are dissolved in a sufficient amount of double-distilled water, and the remaining amount of distilled water is added. The solution is then filtered until free from suspended particles, and the filtrate is filled into 1 cc-ampules under aseptic conditions. The ampules are finally sterilized and sealed. The contents of each ampule are an injectable dosage unit composition containing 5.0 mgm of the active ingredient.

Any one of the other compounds embraced by formulas I and Ia or a non-toxic, pharmacologically acceptable acid addition salt thereof may be substituted for the particular active ingredient in Examples 55 through 58. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

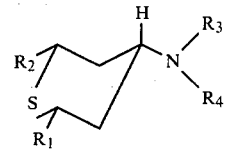

or

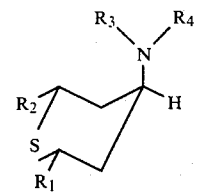

wherein $R_1$ and $R_2$ are each phenyl; mono-, di- or tri-substituted phenyl, where the substituents are halogen, methyl or methoxy; thienyl; or furyl;

$R_3$ is hydrogen or alkyl of 1 to 3 carbon atoms; and $R_4$ is alkyl of 1 to 3 carbon atoms; or $R_3$ and $R_4$, together with each other and the nitrogen atoms to which they are attached, form a piperidino, 4-amino-piperidino, 4-(lower alkyl-amino)-piperidino, piperazino, 4-(alkyl of 1 to 2 carbon atoms)-piperazino or morpholino radical; or a non-toxic, pharmacologically acceptable acid addition salt thereof.

2. A compound of claim 1 where $R_1$ and $R_2$ are each phenyl, chloro-phenyl, bromo-phenyl, fluoro-phenyl, dichloro-phenyl, methoxy-phenyl, trimethoxy-phenyl, thienyl or furyl;

$R_3$ is hydrogen or alkyl of 1 to 3 carbon atoms; and $R_4$ is alkyl of 1 to 3 carbon atoms; or $R_3$ and $R_4$, together with each other and the nitrogen atom to which they are attached, form a piperidino, 4-amino-piperidino, 4-(lower alkyl-amino)-piperidino, piperazino, 4-(alkyl of 1 to 2 carbon atoms)-piperazino or morpholino radical;

or a non-toxic, pharmacologically acceptable acid addition salt thereof.

3. A compound of claim 1, where $R_1$ and $R_2$ are each phenyl; mono-, di- or tri-substituted phenyl, where the substituents are halogen, methyl or methoxy; thienyl; or furyl;

$R_3$ is hydrogen or alkyl of 1 to 3 carbon atoms; and $R_4$ is alkyl of 1 to 3 carbon atoms;

or a non-toxic, pharmacologically acceptable acid addition salt thereof.

4. A compound of claim 1, which is 4a-dimethylamino-2,6-bis-(4-methoxy-phenyl)-tetrahydrothiopyran or a non-toxic, pharmacologically acceptable acid addition salt thereof.

5. A compound of claim 1, which is 4e-dimethylamino-2,6-bis-(4-methoxy-phenyl)-tetrahydrothiopyran or a non-toxic, pharmacologically acceptable acid addition salt thereof.

6. A compound of claim 1, which is 4a-methylamino-2,6-bis-(4-methoxy-phenyl)-tetrahydrothiopyran or a non-toxic, pharmacologically acceptable acid addition salt thereof.

7. A compound of claim 1, which is 4e-methylamino-2,6-bis-(4-methoxy-phenyl)-tetrahydrothiopyran or a non-toxic, pharmacologically acceptable acid addition salt thereof.

8. A compound of claim 1, which is 4a-dimethylamino-2-(4-chloro-phenyl)-6-phenyl-tetrahydrothiopyran or a non-toxic, pharmacologically acceptable acid addition salt thereof.

9. A compound of claim 1, which is 4e-dimethylamino-2-(4-chloro-phenyl)-6-phenyl-tetrahydrothiopyran or a non-toxic, pharmacologically acceptable acid addition salt thereof.

10. A compound of claim 1, which is 4a-dimethylamino-2-(4-methoxy-phenyl)-6-phenyl-tetrahydrothiopyran or a non-toxic, pharmacologically acceptable acid addition salt thereof.

11. A compound of claim 1, which is 4e-dimethylamino-2-(4-methoxy-phenyl)-6-phenyl-tetrahydrothiopyran or a non-toxic, pharmacologically acceptable acid addition salt thereof.

12. An antidepressant pharmaceutical dosage unit composition consisting essentially of an inert pharmaceutical carrier and an effective antidepressant amount of a compound of claim 1.

13. The method of preventing or relieving depression in a warm-blooded animal in need thereof, which comprises perorally, parenterally or rectally administering to said animal an effective antidepressant amount of a compound of claim 1.

* * * * *